United States Patent
Tang et al.

(10) Patent No.: US 12,240,932 B2
(45) Date of Patent: Mar. 4, 2025

(54) PHOTOCURABLE HYDROPHILIC POLYMER, AND COATING COMPOSITION, HYDROPHILIC LUBRICATING COATING AND ARTICLE BASED ON THE SAME

(71) Applicant: JIANGSU BIOSURF BIOTECH CO., LTD., Suzhou (CN)

(72) Inventors: Zengchao Tang, Suzhou (CN); Jiehua Lei, Suzhou (CN)

(73) Assignee: JIANGSU BIOSURF BIOTECH CO., LTD., Jiangsu (CN)

( * ) Notice: Subject to any disclaimer, the term of this patent is extended or adjusted under 35 U.S.C. 154(b) by 969 days.

(21) Appl. No.: 17/265,009

(22) PCT Filed: Jul. 4, 2019

(86) PCT No.: PCT/CN2019/094679
§ 371 (c)(1),
(2) Date: Feb. 1, 2021

(87) PCT Pub. No.: WO2020/024763
PCT Pub. Date: Feb. 6, 2020

(65) Prior Publication Data
US 2021/0309781 A1    Oct. 7, 2021

(30) Foreign Application Priority Data
Aug. 2, 2018  (CN) .......................... 201810870339.5

(51) Int. Cl.
| | | |
|---|---|---|
| *C08F 283/06* | (2006.01) | |
| *A61L 29/08* | (2006.01) | |
| *A61L 29/14* | (2006.01) | |
| *C09D 151/08* | (2006.01) | |

(52) U.S. Cl.
CPC ........ *C08F 283/065* (2013.01); *A61L 29/085* (2013.01); *A61L 29/14* (2013.01); *C09D 151/08* (2013.01); *A61L 2400/10* (2013.01)

(58) Field of Classification Search
CPC .... C08F 283/065; A61L 29/085; A61L 29/14; A61L 2400/10; C09D 151/08
See application file for complete search history.

(56) References Cited

U.S. PATENT DOCUMENTS

| | | |
|---|---|---|
| 10,005,717 B2 | 6/2018 | Gevaert et al. |
| 2014/0335326 A1 | 11/2014 | Gevaert et al. |
| 2015/0132544 A1 | 5/2015 | Kano et al. |

FOREIGN PATENT DOCUMENTS

| | | |
|---|---|---|
| CN | 103048883 A | 4/2013 |
| CN | 103209717 A | 7/2013 |
| CN | 103289499 A | 9/2013 |
| CN | 103703030 A | 4/2014 |
| CN | 102947376 B | 4/2015 |
| CN | 104761661 A | 7/2015 |
| CN | 101365501 B | 12/2015 |
| CN | 105732848 A | 7/2016 |
| WO | WO 2014030515 A1 | 2/2014 |

OTHER PUBLICATIONS

International Search Report for PCT/CN2019/094679, dated Oct. 22, 2019, 4 pages.

*Primary Examiner* — Catherine S Branch
*Assistant Examiner* — Andrea Wu
(74) *Attorney, Agent, or Firm* — Fox Rothschild LLP

(57) ABSTRACT

A photocurable hydrophilic polymer, coating composition and hydrophilic lubricating coating based on the same are provided. The photocurable polymer is formed by copolymerization of a polymerizable photosensitive monomer and a hydrophilic monomer. The photosensitive monomer comprises: 1) units containing a photosensitive structure; 2) units containing a tertiary amine co-initiator structure; and 3) units containing and unsaturated bond. The units containing the photosensitive structure are at least connected with the units containing the tertiary amine co-initiator structure through —OC(=O)—, and the units containing the unsaturated bond structure are connected with the units containing the photosensitive structure through the units containing the tertiary amine co-initiator structure. The photocurable hydrophilic polymer has a high photocurable efficiency, a simple preparation process, a high production efficiency, less environmental pollution, and hardly any cross-linking. By curing the coating composition, a hydrophilic coating with high firmness, high lubricity, excellent biosafety and compatibility can be obtained.

20 Claims, No Drawings

PHOTOCURABLE HYDROPHILIC POLYMER, AND COATING COMPOSITION, HYDROPHILIC LUBRICATING COATING AND ARTICLE BASED ON THE SAME

FIELD OF THE INVENTION

The present invention belongs to the field of the photocuring technology, in particular to a photocurable hydrophilic polymer and a coating composition based thereon, and also relates to the field of hydrophilic lubricating coatings, which can be used in medical devices such as catheters/guide wires.

BACKGROUND OF THE INVENTION

With the development of medical technology, the treatment of diseases through minimally invasive methods, such as interventional treatment, is increasingly favored by medical staff and patients. Many interventional medical devices, such as cardiovascular system guide wires/catheters, urinary system catheters, digestive system catheters, etc., need to be inserted into patients' body and directly contact with patients' tissues during use. Untreated guide wires/catheters usually have lower surface lubricity, leading to a great resistance, which easily causes discomfort and tissue damage to the patients and operation inconvenient to the medical staff when inserting or withdrawing from the body. Therefore, proper lubrication technology needs to be developed to improve the surface lubrication of medical guide wires/catheters.

At present, a commonly used lubrication method is coating the guide wire/catheter with lubricants (such as paraffin oil, silicone oil, Vaseline, etc.) before using, but since lubricants cannot be stabilized on the surface of the guide wire, the tissue is still easily damaged. Perfluorinated ethylene propylene and other materials are used to cover the catheter, which improves the lubricity of the catheter to a certain extent, but the lubricity of the catheter with such a coating is still insufficient to avoid body damage. Therefore, methods of forming more lubricious hydrophilic coating on the surface of the guide wire/catheter are investigated.

Patent Document 1 discloses a process for preparing a composition including a hydrophilic polymer, a polyelectrolyte, a photoinitiator and a carrier liquid. The composition can form a lubricating coating under ultraviolet light. However, not adding effective cross-linking component to the composition is likely to cause insufficient cross-linking and weak coating. At the same time, using small molecular photoinitiators, which causes odor and easy fragment migration, also reduces the biological safety and comprehensive performance of the coating.

Patent Document 2 discloses a hydrophilic coating containing polyelectrolyte, in which a clear cross-linking component polyethylene glycol diacrylate is added to ensure the cross-linking extent and firmness of the coating. However, a small molecule photoinitiator is used in this composition, and the problem of the migration of small molecules and fragments is still existed.

Patent Document 3 discloses a preparing method and a using method of coatings containing photoactive hydrophilic resins and photoactive hydrophilic cross-linking agents. Small molecule photoinitiators are polymerized with hydrophilic monomers, which can effectively prevent the residue and migration of small molecule initiators, and enhance the coating's firmness as well. The coating can meet the requirement of passing a friction test of after 15 time cycles. However, a certain amount of cross-linking agent needs to be copolymerized with a hydrophilic monomer and a small molecule photoinitiator in this system, which theoretically causes a gel generation problem during polymerization.

Patent Document 4 discloses a hydrophilic coating including a copolymer of N-vinylpyrrolidone and benzophenone vinyl monomers, and the hydrophilic coating has a friction coefficient of no more than 0.2. The small molecule benzophenone initiator is covalently bonded to the polymer chain in the copolymer, which can effectively avoid the migration of small molecules. However, the structure of the benzophenone vinyl monomer used in this copolymer is a (meth)acrylate group connected to a benzophenone group directly. The length of the molecular chain is shorter and the free radicals are not easy to collide. At the same time, the molecular chain does not have an obvious co-initiator structure, leading to a lower initiation efficiency.

Patent Document 1: CN102947376B
Patent Document 2: CN101365501B
Patent Document 3: CN105732848A
Patent Document 4: CN103209717A

SUMMARY OF THE INVENTION

Technical Problem

In order to solve the problems and shortages of the prior art mentioned above, the present invention provides a photocurable hydrophilic polymer and a coating composition based thereon. The photocurable hydrophilic polymer has a high photocuring efficiency, utilizes a simple preparation method, has high production efficiency, results in less environmental pollution, and there is hardly any cross-linking. A hydrophilic coating with high fastness, high lubricity, excellent biosafety and compatibility can be obtained by curing the coating composition.

In addition, the present invention also provides a hydrophilic lubricating coating obtained from the coating composition and articles such as a medical device that include the coating composition.

Additional objects and advantages of the invention will be set forth in part in the following description, or may be obvious from the description, or may be learned through practice of the invention.

Solution to Problem

The present invention provides a photocurable hydrophilic polymer, which is formed by copolymerization of polymerizable photosensitive monomers and hydrophilic monomers; wherein the polymerizable photosensitive monomer comprises: 1) units containing a photosensitive structure; 2) units containing a tertiary amine co-initiator structure; and 3) units containing an unsaturated bond;

Further, the units containing the photosensitive structure are at least connected with the units containing the tertiary amine co-initiator structure through —OC(=O)—, and the units containing the unsaturated bond structure are connected with the units containing the photosensitive structure through the units containing the tertiary amine co-initiator structure.

Preferably, the polymerizable photosensitive monomer has the structure of general formula (I):

general formula (I)

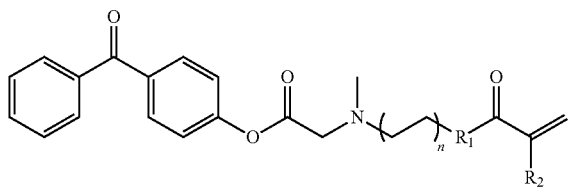

wherein, n is an integer of 1-20, preferably 1 or 2; $R_1$=O or NR, where in R is H, a C1-C20 straight alkyl group or a C3-C20 branched alkyl group; and $R_2$=H, a C1-C20 straight alkyl group or a C3-C20 branched alkyl group.

Preferably, the hydrophilic monomer includes unsaturated carboxylic acid, unsaturated carboxylate, unsaturated carboxylic acid ester, unsaturated acid hydroxyalkyl ester, unsaturated acid polyether ester, unsaturated anhydride, unsaturated amide, unsaturated lactam and alkylene oxide, or a combination thereof; preferably, the hydrophilic monomer is selected from (meth)acrylic acid, (meth)acrylamide, vinyl pyrrolidone, hydroxyethyl (propyl) (meth)acrylate, polyethylene glycol methyl ether (meth)acrylate, dimethylacrylamide, or a combination thereof; more preferably, the hydrophilic monomer is selected from polyethylene glycol methyl ether acrylate.

Preferably, the molar fraction of polymerizable photosensitive monomer in the hydrophilic polymer is 0.05-10%, preferably 0.5-5%, and further preferably 0.8-1.5%.

Preferably, the number average molecular weight of photocurable hydrophilic polymer is 2,000-1,500,000, preferably 50,000-600,000, further preferably 150,000-300,000.

Preferably, the present invention provides a coating composition, including:
1) a photocurable hydrophilic polymer according to the present invention, which has a mass fraction of 0.1-20% based on the total amount of the coating composition, preferably 1-10%, further preferably 3-5%; and
2) a solvent, which has a mass fraction of 60-99.9% based on the total amount of the coating composition, preferably 90-99%, and more preferably 95-98%.

Preferably, the solvent includes water, low molecular weight alcohol, N, N-dimethylformamide, N,N-dimethylacetamide, dimethylsulfoxide, acetone, phenol, or a combination thereof, preferably the solvent is a mixture of water and ethanol, and more preferably, the volume ratio of water and ethanol is 2:3-3:2.

More preferably, the invention provides a hydrophilic lubricating coating obtained by curing the coating composition above.

In addition, the present invention also provides an article, such as a medical device, comprising at least one layer of the hydrophilic lubricating coating as described above.

Advantageous Effects of Invention

The present invention has the following advantageous effects compared with the prior art:
1. By using a new polymerizable photosensitive monomer with a longer linking chain and a tertiary amine structure that can participate in co-initiation in the present invention, the prepared photocurable hydrophilic polymer has a high UV curing efficiency and firmly gelling property.
2. The photocurable hydrophilic polymer in the invention has the advantages of simple synthesis, easy control of reaction conditions and hardly any cross-linking.
3. A coating composition for further preparing a photocurable hydrophilic lubricating coating is prepared based on the curable polymer of the present invention. Compared with other existing photocurable coatings, the photocurable polymer used in the present invention contains a photosensitive structural unit itself, so it is unnecessary to add extra small molecular photoinitiators in the coating composition, which can overcome the problems associated with residue and migration of small molecule photoinitiators in the coating. It also has excellent biological safety and compatibility, and is suitable for use in the medical field.
4. The coating composition can form a uniform and stable hydrophilic lubricating coating through a simple continuous dip coating-photo curing process, which feels like lotion after wetting when being coated on the surface of medical equipment. The coating does not fall off and the lubricity did not decrease after 30 time cycles during a friction test in a simulated human tissue environment, proving that the coating is firm.
5. By regulating the types of hydrophilic monomers, the molar ratio of polymerizable photosensitive monomers to hydrophilic monomers, and the molecular weight of the photocurable hydrophilic polymers, the best polymer for preparing the hydrophilic coating is found.
6. By selecting the type and content of each component of the coating composition, a hydrophilic coating with high firmness and lubricity is prepared in the present invention.

DETAILED DESCRIPTION

The technical solutions of the present invention will be described in detail below in combination with the embodiments. Reference will now be made to embodiments of the invention. Each embodiment is provided by way of explanation of the invention, and not as a limitation of the invention. For example, features illustrated or described as part of one embodiment can be combined with another embodiment to yield still another embodiment. It is intended that the present invention include these and other modifications and variations to the embodiments described herein.

A "monomer" within the meaning of the invention is any chemical substance which can be characterized by a chemical formula, bearing polymerizable groups (including (meth) acrylate groups) which can be polymerized to oligomers or polymers thereby increasing the molecular weight. The molecular weight of monomers can usually simply be calculated based on the chemical formula given.

In the following, when a part of a molecule is described as "optionally substituted" or "substituted", it is meant that said part may be substituted by one or more substituents selected from: $C_1$-$C_6$ linear, branched or cyclic alkyl, aryl, —OH, —CN, halogens, amines, amides, alcohols, ethers, thioethers, sulfones and derivatives thereof, sulfoxides and derivatives thereof, carbonates, isocyanates, nitrates and acrylates.

The meaning of the term "unit" in the present invention includes not only functional groups (such as photosensitive groups, quaternary ammonium salt groups, unsaturated groups), but also additional chemical groups, such as alkyl, alkylene, etc., which have little influence on the functional groups.

The meaning of the term "polymer" in the present invention is a molecule comprising two or more repeating units. In particular it may be composed of two or more monomers which may be the same or different. As used herein, the term includes oligomers and prepolymers. The meaning of the term "molecular weight" in the present invention is the number average molecular weight ($M_n$), and the $M_n$ is defined as the $M_n$ determined by light scattering (optionally in combination with Size Exclusion Chromatography SEC).

The meaning of the term "curing" in the present invention is understood to refer to physical or chemical hardening or solidifying by any method, for example heating, cooling, drying, crystallization or curing as a result of a chemical reaction, such as radiation-curing, heat-curing or curing by adding curing molecules or initiators.

The meaning of the term "UV curing" in the present invention can be taken place by an exemplary method as follows: a photoinitiation process takes place through light irradiation or UV irradiation in the wavelength range from 100 nm to 600 nm. Irradiation sources which may be used are sunlight or artificial lamps or lasers. For example, high-pressure, medium pressure or low-pressure mercury lamps and xenon and tungsten lamps are advantageous. Similarly, lasers based on excimer, solid-state and diode are advantageous. Diode-based light sources in general are advantageous for initiating the chemical reactions.

First Embodiment

The first embodiment of the present invention provides a photocurable hydrophilic polymer, which is formed by copolymerization of polymerizable photosensitive monomers and hydrophilic monomers. The photosensitive structural unit of the photocurable hydrophilic polymer can be used as a macromolecular photoinitiator. Therefore, it is unnecessary to add an extra small molecular photoinitiator when being prepared into a coating composition, which can overcome the problems associated with residue and migration of small molecule photoinitiators in the coating. It has excellent biological safety and compatibility, and is suitable for use in the medical field.

Polymerizable Photosensitive Monomer

The polymerizable photosensitive monomer comprises: 1) units containing a photosensitive structure; 2) units containing a tertiary amine co-initiator structure; 3) units containing an unsaturated bond; wherein the units containing the photosensitive structure are at least connected with the units containing the tertiary amine co-initiator structure through —OC(=O)—, and the units containing the unsaturated bond structure are connected with the units containing photosensitive structure through the units containing the tertiary amine co-initiator structure.

The photosensitive structure-containing unit of the present invention is derived from an aryl ketone type photoinitiator structure, which includes a carbonyl functional group and one or more aromatic rings. The aryl ketone structure may further include a sulfur atom as well. The photosensitive unit can be derived from but not exclusively limited to substituted or unsubstituted benzophenone, acetophenone, thioxanthone, xanthone, fluorenone, and derivatives thereof. The unit typically containing a photosensitive structure may be a benzophenone having the general formula (II) in one embodiment of the invention:

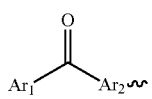

general formula (II)

Wherein, $Ar_1$ and $Ar_2$ are independently selected from the same or different optionally substituted aryl groups, and where the wavy line indicates that it is connected to the structural unit containing the tertiary amine co-initiator through a linking group. Preferably, both $Ar_1$ and $Ar_2$ may be optionally substituted phenyl, and further preferably both of them are phenyl. The structural unit containing the tertiary amine co-initiator is preferably in the para position of $Ar_2$, which provides the greatest opportunity for electronic interaction with the carbonyl group and thus forms the maximum amount of stabilization of free radicals.

It is found that when a benzophenone unit is used as the photosensitive structural unit of the present invention, better photoinitiation efficiency can be achieved compared with a small molecule photosensitizer or a combination thereof.

The unit with the unsaturated bond contained in the polymerizable photosensitive monomer may be a polymerizable group containing a double bond. Such reactive groups can make the photosensitive structural units combine with the main chain of the polymer in the form of repeating units by free radical polymerization.

In the present invention, the unit with the unsaturated bond may be selected from a unit with a (meth)acryloyl group. For example, the unit may be (meth)acrylate or (meth)acrylamide. The presence of polymerizable groups can overcome the problems of toxicity and high mobility of conventional small molecule photoinitiators, promote the anchoring of photoinitiators in the polymer network, and also improve material properties by copolymerizing with other monomers, and inhibit the unexpected volatilization caused by the residue of small molecule photoinitiators as well.

The unit containing the tertiary amine co-initiator structure can contain a tertiary amine group, and may further contain several alkylene groups. Under UV irradiation, tertiary amines have the ability to capture protons from carbon atoms adjacent to the amino nitrogen, which can effectively act as H donors for reactive functional groups. Reactive groups that can initiate polymerization or cross-linking can be produced in this way.

The photosensitive structural unit is connected to the tertiary amine co-initiator structure through an ester bond (—OC(=O)—) on the aromatic ring, and the unit with the unsaturated bond is connected to the unit of the photosensitive structure through the tertiary amine co-initiator structure unit. In a preferred embodiment of the present invention, the nitrogen atom in the tertiary amine structure is connected to the above (meth)acryloyloxy or (meth)acrylamide and the ester bond on the aromatic ring of the photosensitive structural unit via an alkylene group, respectively.

In a preferred embodiment of the present invention, the polymerizable photosensitive monomer containing tertiary amine co-initiator has the following structure:

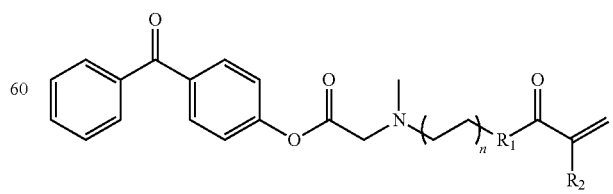

wherein, n is an integer of 1-20, preferably 1 or 2; $R_1$=O or NR, wherein R is H, a C1-C20 straight alkyl group or a C3-C20 branched alkyl group; and R$_2$=H, a C1-C20 straight alkyl group or a C3-C20 branched alkyl group.

In the present invention, the unit of the photosensitive structure is connected with the nitrogen atom in the structure unit containing the tertiary amine co-initiator by a specific linking group, i.e. an ester group and a methylene group. The connection provides the greatest opportunity for the interaction between the two units, which can produce more free radical active species faster and improve the initiation efficiency.

Further preferably, suitable polymerizable photosensitive monomers according to the present invention include one or more compounds of the following structure:

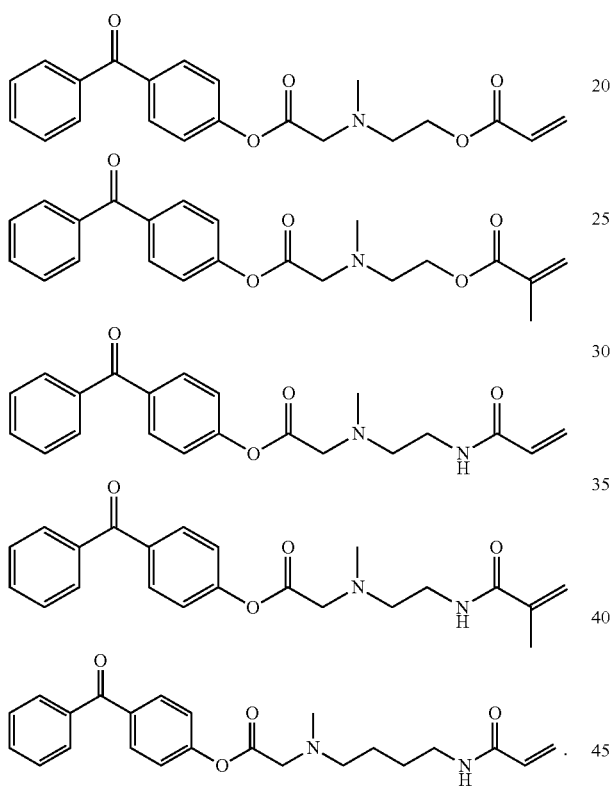

The polymerizable photosensitive monomer of the present invention is obtained by the reaction between the (meth) acrylate containing alkyl amino group or the (meth) acrylamide containing alkyl amino group and a substance which has a halogenated ester group and a photosensitive structure.

The reaction process of the polymerizable photosensitive monomer of the present invention is as follows:

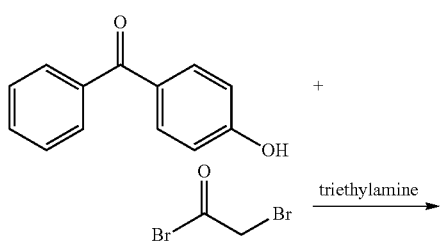

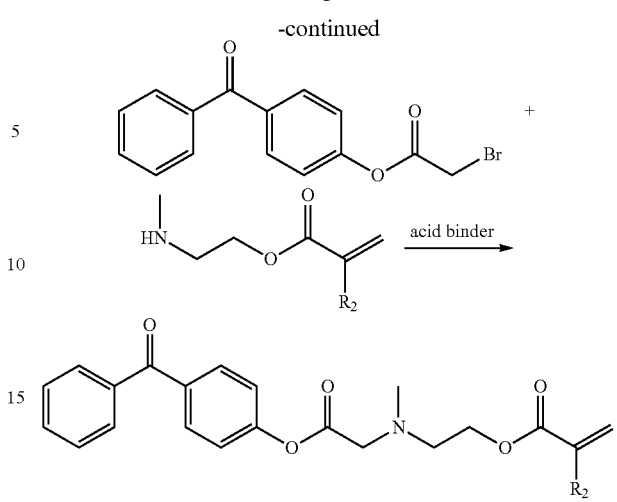

wherein, R$_2$=H or a C1-20 straight alkyl group or a C3-20 branched alkyl group. Or,

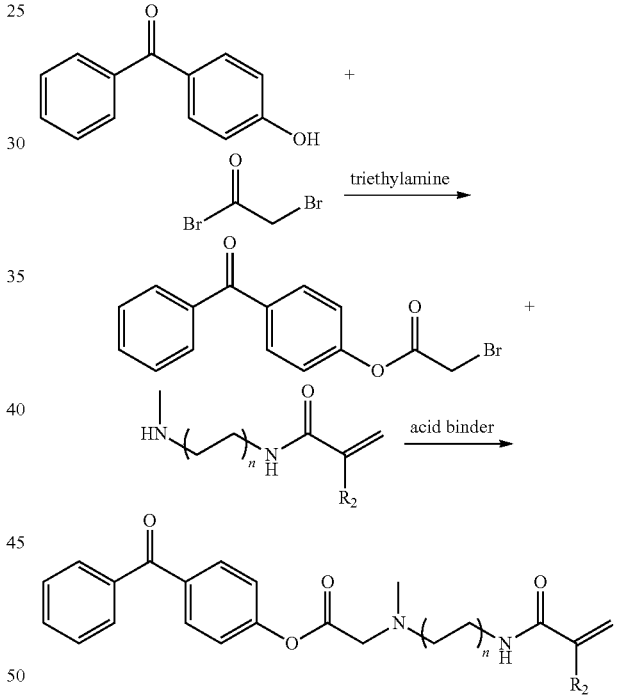

wherein, R$_2$=H or a C1-20 straight alkyl group or a C3-20 branched alkyl group, and where n is an integer of 1-20.

It is found that the molar fraction of the polymerizable photosensitive monomer in the polymer, i.e., the copolymer, will affect the lubricity of the hydrophilic coating prepared by the polymer. If the molar fraction is too high, the content of hydrophilic monomers will be relatively reduced, leading to a poor initial lubricity and high friction of the obtained hydrophilic coating. If the molar fraction is too low, the curing efficiency will be affected, and as the number of friction test cycles is increased, the friction of the coating increases rapidly. In the present invention, the molar fraction of the water-soluble polymerizable photosensitive monomer in the copolymer is 0.05-10%, preferably 0.5-5%, and further preferably 0.8-1.5%. In a preferred embodiment of the present invention, the molar fraction of the water-soluble polymerizable photosensitive monomer in the copolymer is 1%, which results in a coating having the lowest frictional force (0.12N), and the frictional force hardly increases with an increase in the number friction test cycles, even after more than 30 friction cycles.

Hydrophilic Monomer

Hydrophilic monomers refer to monomers that can dissolve 1 g or more in 100 g water at 25° C. Hydrophilic monomers are mainly used to provide hydrophilicity to the polymer.

Hydrophilic monomers may include, but are not limited to, unsaturated carboxylic acids or carboxylate, unsaturated carboxylic acid ester, unsaturated acid hydroxyalkyl ester, unsaturated acid polyether ester, unsaturated acid anhydride, unsaturated amide, unsaturated lactam, alkylene oxide, or a combination thereof; preferably, hydrophilic monomers are selected from (meth)acrylic acid, (meth)acrylamide, vinylpyrrolidone, (meth)hydroxyethylene(propylene) acrylate, polyethylene glycol methyl ether (methyl) acrylate, dimethylacrylamide, or a combination thereof; and more preferably, hydrophilic monomers are selected from polyethylene glycol methyl ether acrylate.

It is found that when using polyethylene glycol methyl ether acrylate ($M_n$=480, Sigma-Aldrich) as the hydrophilic monomer, the obtained hydrophilic coating has an improved lubricating effect, which is prominently reflected in the low friction and the friction is almost unchanged with the increase in the number of friction test cycles, where the level of friction can be even lower than the first cycle after subsequent cycles.

Polymerization

The photocurable polymer in the present invention is prepared by a radical polymerization method, including but not limited to ordinary radical polymerization and living/controlled radical polymerization. Preferably, the curable hydrophilic polymer is prepared by ordinary radical polymerization methods. The photocurable polymer is prepared in a certain medium, including but not limited to solution polymerization, emulsion polymerization, inverse emulsion polymerization, suspension polymerization and bulk polymerization. From the perspective of easy operation, the photocurable polymer is prepared by solution polymerization preferably. From an environmental protection perspective, the photocurable polymer is prepared in an aqueous solution more preferably. In one embodiment of the present invention, polymerizable photosensitive monomers and hydrophilic monomers are dissolved in water, radical initiators are added to the system, the oxygen is removed, and the reaction is performed at a specific temperature. When the reaction is completed, the reaction solution is precipitated with 95% ethanol, and the obtained precipitate is dried in an oven to obtain a photocurable polymer.

In the polymerization reaction, the radical initiator refers to a substance that can produce free radicals under the activation energy, including thermally activated initiators, such as organic peroxides, organic hydrogen peroxides, and azo compounds. Representative examples of these initiators include, but are not limited to, benzoyl peroxide, tert butyl peroxybenzoate, diisopropyl peroxydicarbonate, cumene hydroperoxide, azodiisobutyronitrile, etc. In a preferred embodiment of the present invention, the free radical initiator is azodiisobutyronitrile. The thermal initiator is usually used in the amount of 0.01 to 5% by mass of the monomers, preferably 0.05 to 0.15%.

In order to reduce mobility, the number average molecular weight of the photocurable polymer is at least 2000, and a relatively high molecular weight photocurable polymer is preferred. But for ease of application of the coating, it is preferably 1.5 million or less. It is found that the molecular weight of the photocurable polymer will affect the lubricity of the hydrophilic coating as well. In order to obtain a hydrophilic coating with good lubricity after multiple time cycles, the number average molecular weight of the photocurable polymer is preferably 50,000-600,000, and further preferably 150,000-300,000.

Second Embodiment

The second embodiment of the present invention provides a coating composition, including:
1) a photocurable polymer according to the invention, which has a mass fraction of 0.1-20%, preferably 1-10%, further preferably 3-5%; and
2) solvent, which has a mass fraction of 60-99.9%, preferably 90-99%, and more preferably 95-98%.

Photocurable Polymer

The photocurable polymer is a polymer according to the first embodiment of the present invention, which has photoinitiated activity. Since the photocurable polymer itself is hydrophilic, it can be directly prepared into a coating composition and coated on the surface of a substrate to obtain a hydrophilic coating by photocuring. Another hydrophilic polymer can also be added optionally. The amount of the photocurable polymer has an important influence on the curing speed of the coating composition, as well as the firmness and the lubricity of the coating. In the present invention, the mass fraction of the photocurable polymer in the coating composition is 0.1-20%, further preferably 1-10%, more preferably 3-5% from the perspective of improving the lubricity.

Solvent

Any solvent that allows a coating composition with hydrophilicity to be coated on the surface is satisfactory. Preferably, the solvent is a single or mixed solvent that can dissolve the photocurable hydrophilic polymer and form a homogeneous solution of the hydrophilic polymer.

Solvents include water, low molecular weight alcohols (methanol, ethanol, isopropanol, butanol, pentanol, ethylene glycol, propylene glycol, glycerol, etc.), N,N-dimethylformamide, N,N-dimethylacetamide, dimethylsulfoxide, acetone, phenol, or a combination thereof. Preferably, the solvent is a single or mixed solvent that can dissolve the photocurable hydrophilic polymer to form a homogeneous solution. Preferably, the solvent is a mixture of water and ethanol, and further preferably, the volume ratio of water to ethanol is 2:3-3:2.

The mass fraction of the solvent in the coating composition is 60%-99.9%, preferably 75-98%, further preferably 90-98%.

Optional Components

Lubricating additives such as surfactants, waxes, lubricants, soaps and detergents can also be added to the coating composition as needed. These lubricant additives will not increase the osmotic concentration of the coating, but can increase the wetting lubricity and reduce the adhesion. Their low solubility in water helps to keep them in the coating. Other additives may include support polymers, polyelectrolytes, wetting agents, leveling agents, defoamers, film forming additives, thickeners, pigments, antibacterial agents, colorants, surfactants, etc. In the specific embodiment of the present invention, good lubricity and firmness of the coating composition can be obtained without adding additional optional components except for photocurable polymer, solvent and optional hydrophilic polymer.

Preparation

The coating composition of the present invention can be prepared by adding the photocurable polymer and the optional hydrophilic polymer to a mixed solvent prepared in advance in the dark, stirring and dissolving the mixture overnight. The resulting solution is colorless and clear.

Third Embodiment

The third embodiment of the present invention provides a hydrophilic lubricating coating, which is obtained by curing the coating composition described in the second embodiment of the present invention.

The hydrophilic lubricating coating can be formed as follows:

The coating composition of the present invention is coated on at least one surface of a substrate; and then the coating composition is cured by exposing the composition to electromagnetic radiation, preferably ultraviolet radiation, to excite the photosensitive structural units in the photocurable polymer.

In general, the coating composition can be applied to the substrate by, for example, dip-coating. Other methods of application include spraying, washing, vapor deposition, brushing, rolling and other methods known in the art. Curing can be performed at any suitable temperature, depending on the substrate, provided that the mechanical or other properties of the substrate are not adversely affected to an unacceptable degree. Preferably, the ultraviolet light intensity during curing is 5-25 mW/cm$^2$, and the curing time is 2-7 minutes, preferably 3-5 minutes. The thickness of the hydrophilic coating may be controlled by altering the soaking time, drawing speed, or viscosity of the coating composition and the times of carrying out the various steps. Typically the thickness of a dry hydrophilic coating on a substrate ranges from 0.1-200 μm, preferably 0.5-100 μm, more preferably 1-20 μm.

In one embodiment of the present invention, the substrate can be a catheter that is immersed in a cylinder containing the coating liquid composition of the present invention for 0.5-2 min, and pulled at a speed of 0.5-1 cm/s. The catheter with the coating liquid is irradiated by an ultraviolet lamp for 3-5 minutes for a curing treatment, and the cured sample is air dried to obtain a catheter with a hydrophilic lubricant coating.

Fourth Embodiment

The fourth embodiment of the present invention provides an article including at least one layer of the hydrophilic lubricating coating according to the third embodiment of the present invention.

According to the above, various articles with the hydrophilic lubricating coating according to the present invention can be obtained by applying and curing the coating. The shape of the article is not limited and can include films, sheets, rods, tubes, molded parts, fibers, fabrics and particles. The hydrophilic lubricating coating can be applied directly to the surface of the product, or to a pre-treated or coated surface. The pre-treatment method can include wiping the surface of the article with ethanol and then drying it.

In one embodiment of the invention, the hydrophilic lubricating coating according to the invention is applied to a biomedical substrate such as a medical device to reduce friction under wet conditions. The coated medical device can be inserted into various living tissues and medium-contained physiological solutions. These tissues include, for example, mucous membranes such as urethras, blood vessels, hearts, kidneys, lungs, throats, and eyes. The invention provides medical devices that feel as if they have been lubricated with lotion, so that they can be easily inserted into body tissues or cavities, and can maintain hydrophilicity and lubricity after being in contact with tissues, such as mucous membranes for a long time, and so that they can easily be taken out. The coating does not fall off and the lubricity did not decrease after 30 time cycles during a friction test in a simulated human tissue environment, proving that the coating is firm. In one specific embodiment of the present invention, the friction force of coating does not significantly increase after 30 time cycles during a friction test, which reflects its excellent firmness. It is known in the art that an increased frictional force of the coating means that the coating falls off with poor fastness, while on the contrary, a decreased frictional force means that the coating is stable and firm.

The "medical device" in the present invention should be interpreted in a broad sense. The medical device can be an implantable device or an extracorporeal device. The device can be of short-term temporary use or of long-term permanent implantation. Suitable examples of medical devices are catheters, guide wires, endoscopes, laryngoscopes, feeding tubes, drainage tubes, medical wires, condoms, barrier coatings such as for gloves, stents, stent grafts, anastomotic connectors, extracorporeal blood catheters, membranes such as those used in dialysis, blood filters, circulation aids, wound dressings, urine collection bags, ear tubes, intraocular lens, and any tubes used in minimally invasive surgery. Typically, the medical device is selected from catheters, guide wires, endoscopes, laryngoscopes, feeding tubes, drainage tubes, and medical wires. Articles that are particularly suitable to be used in the present invention include catheters (e.g., intermittent catheters, balloon catheters, PTCP catheters, stent delivery catheters), guide wires, wires, syringes, contact lenses, medical tubes and stents, and other implants based on metals or polymers. In particular, the present invention is suitable for catheters/guide wires of various materials, including polyurethane, silicone rubber, latex, nylon, polyvinyl chloride, Pebax, nickel-titanium alloy, etc.

EXAMPLES

The following examples are used to illustrate the present invention, and those skilled in the art can understand that each example is only an exemplary description, not an exhaustive description.

Test Methods

The lubricity of the present invention is tested using a clip-type friction tester. In particular, the pipe is clamped by double clamps which are placed in deionized water. A certain force is applied through the clamps to test the force required to pull the pipe. The ratio of the certain force to the clamping force is the friction coefficient, which is used to evaluate the lubricity of the coating. The clamping force used is 300 g, the pulling speed is 10 mm/s, and the test repeats for 30 time cycles.

Example 1

Step 1: Synthesis of Polymerizable Photosensitive Monomers 3.35 g (26 mmol) of 2-(methylamino) ethyl acrylate, 3.95 g (28 mmol) of potassium carbonate and 0.02 g of hydroquinone were dissolved in 30 mL of acetonitrile and placed in a 100 mL flask, heated and refluxed for 2 h. 20 mL of 4-benzoylphenyl bromoacetate (8.3 g, 26 mmol) in acetonitrile was slowly dropped into the flask. The addition was completed within 1 h. The reaction was carried out at 80° C. for 10 h. After the reaction, the crude product was cooled to room temperature and dissolved in dichloromethane, washed in sequence with saturated salt water, hydrochloric acid (1M) and saturated sodium bicarbonate twice, dried by anhydrous magnesium sulfate overnight, then filtered, after which the solvent was dried by SFD, and the crude product was purified by column chromatography using ethyl acetate and n-hexane as the eluent. 5.12 g light yellow solid was obtained, as shown in formula 1. NMR results: 2.24 ppm (s, 3H, CH3), 2.58 ppm (m, 2H, CH2), 3.52 ppm (s, 2H, CH2), 4.46 ppm (m, 2H, CH2), 5.83-6.42 ppm (m, H, CH2), 6.12 ppm (m, H, CH), 7.43-7.82 ppm (m, 9H, benzene ring).

Formula 1

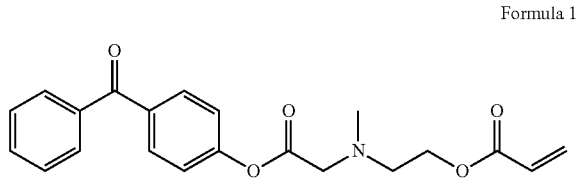 [SMILES: C=CC(=O)OCCN(C)CC(=O)Oc1ccc(C(=O)c2ccccc2)cc1]

Step 2: Synthesis of Photocurable Hydrophilic Polymer 47.52 g (0.099 mol) of polyethylene glycol methyl ether acrylate, 0.367 g (0.001 mol) of the polymerizable photosensitive monomer prepared in step 1, and 0.048 g of azobisisobutyronitrile were added to a 500 mL round bottom flask. Then 150 mL of deionized water and 80 mL of methanol were added and dissolved by mechanical stirring. $N_2$ was purged for 30 minutes to remove the oxygen, and the reaction flask was heated in a 65° C. oil bath to start the reaction. After 6 hours, the reaction solution was removed and cooled to room temperature, and precipitated in 95% ethanol. The precipitate was dried in a vacuum oven at 35° C. in the dark for 36 hours. The number average molecular weight Mn of the obtained photocurable polymer measured by GPC was 254 k, and the PDI was 2.21.

Step 3: Preparation of the Coating Composition 3 g of the photocurable hydrophilic polymer ($M_n$=254 k, mole fraction of polymerizable photosensitive monomer=1%) prepared in step 2 was added into a brown bottle, and then 97 g of ethanol/water mixed solvent (volume ratio 1:1) was added and dissolved in the dark with stirring for 24 h. A colorless, clear solution was obtained.

Step 4: Preparation of Hydrophilic Coating and its Products

The surface of a polyurethane catheter (catheter diameter Fr=5.5 mm) was wiped by dust-free papers with 75% ethanol and dried. The catheter was immersed in a cylinder containing the coating solution composition prepared in step 3 for 1 minute, and then pulled out at a speed of 0.5 cm/s. The catheter with the coating solution was irradiated and cured by an ultraviolet lamp for 5 minutes. The intensity of UV light was 10 mW/cm², and the rotation speed of the catheter was 4 rpm. The cured sample was dried in air.

Step 5: Test the Lubricity

The coated catheter obtained in step 4 was observed to avoid obvious unevenness, and placed in a clamp friction tester to test the lubricity. The results are shown in Table 2.

Example 2

The amount of the photocurable hydrophilic polymer in step 3 was changed, and the amount of the ethanol/water mixed solvent was adaptively adjusted. The formulations of the coating composition are shown in Table 1 while other steps are the same as Example 1. The results of lubricity were tested and shown in Table 2.

TABLE 1

Formulations of coating compositions with different mass fractions of photocurable hydrophilic polymer

| Component | Mass fraction |
| --- | --- |
| Example 1 Photocurable hydrophilic polymer ($M_n$ = 254k, Mole fraction of polymerizable photosensitive monomers: 1%) | 0.1-20% |
| Ethanol/water | 80-99.9% |

TABLE 2

Effects of photocurable hydrophilic polymer concentration on coating properties

| Concentration of photocurable hydrophilic polymer/% | Friction force of the first cycle | Friction force of the 30th cycle |
| --- | --- | --- |
| 0.1 | 0.73 | 0.87 |
| 0.5 | 0.44 | 0.53 |
| 1 | 0.37 | 0.45 |
| 2 | 0.26 | 0.35 |
| 3 | 0.12 | 0.14 |
| 4 | 0.11 | 0.13 |
| 5 | 0.09 | 0.14 |
| 7.5 | 0.08 | 0.21 |
| 10 | 0.08 | 0.57 |
| 20 | 0.07 | 0.64 |

As shown in Table 2, when the concentration of photocurable hydrophilic polymer ranged from 3% to 5%, an article with excellent lubricating performance was obtained. In contrast, the initial friction was higher when the amount was 0.1%, and the friction was significantly increased after the 30th cycle's friction test when the amount was increased to 20%.

Example 3

The reaction time and the amount of initiator in step 2 in Example 1 were changed to obtain photocurable hydrophilic polymers with different molecular weights (the molecular weights in Table 4 were rounded). The formulation of the coating composition is shown in Table 3 while the other steps were the same as in Example 1. The results of lubricity were tested and are shown in Table 4.

TABLE 3

Formulations of coating compositions of photocurable hydrophilic polymers with different molecular weights

| Component | Mass fraction |
| --- | --- |
| Photocurable hydrophilic polymer ($M_n$ = 2-1500k, Mole fraction of polymerizable photosensitive | 3% |

TABLE 3-continued

Formulations of coating compositions of photocurable hydrophilic polymers with different molecular weights

| Component | Mass fraction |
|---|---|
| monomers: 1%) | |
| Ethanol/water | 97% |

TABLE 4

Effects of photocurable hydrophilic polymer molecular weight on coating properties

| $M_n$ of photocurable hydrophilic polymer/k | Friction force of the first cycle | Friction force of the 30th cycle |
|---|---|---|
| 2 | 0.60 | 0.82 |
| 20 | 0.55 | 0.78 |
| 50 | 0.36 | 0.33 |
| 100 | 0.19 | 0.21 |
| 150 | 0.14 | 0.15 |
| 250 | 0.12 | 0.14 |
| 300 | 0.11 | 0.10 |
| 600 | 0.09 | 0.45 |
| 1500 | 0.07 | 0.56 |

According to Table 4, a relatively high molecular weight of the photocurable hydrophilic polymer resulted in a reduction in the initial frictional force. Considering the lubricity after the 30th cycle, the molecular weight was most preferably 150 k-300 k.

Example 4

The mole fraction of the polymerizable photosensitive monomer of the copolymer in step 2 in Example 1 was changed. The formulation of the coating composition was shown in Table 5, while other steps were the same as in Example 1. The results of lubricity were tested and are shown in Table 6.

According to Table 6, the molar fraction of the polymerizable photosensitive monomer of the copolymer had a great influence on the lubricity. The mole fraction in the range of 0.8-1.5% showed the best lubricity. The cycle times that could maintain low friction was decreased if the mole fraction was too low.

TABLE 5

Formulations of coating composition of photocurable polymer synthesized by polymerizable photosensitive monomer with different molar fraction

| Component | Mass fraction |
|---|---|
| Photocurable hydrophilic polymer ($M_n$ = 254k, Mole fraction of polymerizable photosensitive monomers: 0.05-10%) | 3% |
| Ethanol/water | 97% |

TABLE 6

Effects of mole fraction of polymerizable photosensitive monomer on coating properties

| Mole fraction of polymerizable photosensitive monomer/% | Friction force of the first cycle | Friction force of the 30th cycle |
|---|---|---|
| 0.05 | 0.17 | 0.93 |
| 0.5 | 0.14 | 0.59 |
| 0.8 | 0.13 | 0.21 |
| 1 | 0.12 | 0.14 |
| 1.5 | 0.13 | 0.14 |
| 3 | 0.24 | 0.23 |
| 5 | 0.33 | 0.35 |
| 10 | 0.45 | 0.51 |

Example 5

In step 2 of Example 1, the hydrophilic monomer polyethylene glycol methyl ether acrylate was replaced with acrylic acid, acrylamide, vinylpyrrolidone, hydroxyethyl acrylate, and dimethylacrylamide to prepare a series of photocurable polymers of similar molecular weights. The formulations of the coating compositions are shown in Table 7, while other steps were the same as in Example 1. The results of lubricity were tested and are shown in Table 8.

According to Table 8, the friction force while using polyethylene glycol methyl ether acrylate was the lowest, while an excellent lubricity can also be obtained using hydroxyethyl acrylate.

TABLE 7

Formulations of photocurable hydrophilic polymer coating composition synthesized by different hydrophilic monomers

| Component | Mass fraction |
|---|---|
| Photocurable hydrophilic polymer (Mn = 210-270k, Mole fraction of polymerizable photosensitive monomers: 1%) | 3% |
| Ethanol/water | 97% |

TABLE 8

Effect of hydrophilic monomers on coating properties

| Hydrophilic monomer | Friction force of the first cycle | Friction force of the 30th cycle |
|---|---|---|
| Acrylic acid | 0.37 | 0.28 |
| Acrylamide | 0.24 | 0.29 |
| Vinyl pyrrolidone | 0.19 | 0.26 |
| Hydroxyethyl acrylate | 0.16 | 0.18 |
| Polyethylene glycol methyl ether acrylate | 0.12 | 0.14 |
| Dimethylacrylamide | 0.31 | 0.32 |

Comparative Example 1

Preparation of 4-benzoyl phenyl acrylate 19.8 g (0.1 mol) of 4-hydroxybenzophenone and 16.6 mL of triethylamine were added to a 500 mL round bottom flask. 200 mL of dichloromethane was added and stirred to dissolve. The reaction solution was cooled in an ice-water-bath for 15 min, and then 9.78 mL of acryloyl chloride was added dropwise to the solution within half an hour. The solution was reacted in the ice-water-bath for 1 h, and then at room temperature for 3 h. Then, the solution was filtered, and the filtrate was washed three times with a saturated sodium bicarbonate solution and three times with a saturated sodium chloride solution. The organic phase was dried over anhydrous magnesium sulfate, concentrated by rotary evaporation, and the product was obtained by column chromatography.

Preparation of hydrophilic polymer containing 4-benzoylphenyl acrylate 47.52 g (0.099 mol) of polyethylene glycol methyl ether acrylate, 0.252 g (0.001 mol) of the 4-benzoyl phenyl acrylate mentioned above, and 0.048 g of azobisisobutyronitrile were added into a 500 mL round bottom flask. Then 150 mL of deionized water and 80 mL of methanol were added and dissolved by mechanical stirring. The solution was purged with $N_2$ for 30 minutes to remove the oxygen, and the reaction flask was heated in a 65° C. oil bath to start the reaction. After 6 hours, the reaction solution was removed and cooled to room temperature, and precipitated in 95% ethanol. The precipitate was dried in a vacuum oven at 35° C. in the dark for 36 hours. The number average molecular weight $M_n$ of the obtained photocurable polymer measured by GPC was 217 k, and the PDI was 2.08.

Curing Experiment 0.1 g of the hydrophilic polymer prepared in Example 1 and Comparative Example 1 were weighed, respectively, and dissolved in 1 mL of water, then irradiated with UV light at 10 mW/cm$^2$ for 2 minutes. The curing states of the two solutions were observed.

The results showed that the coating liquid containing the hydrophilic polymer prepared in Example 1 was cured and formed into glue after irradiation without flowing. The coating liquid containing the hydrophilic polymer prepared in Comparative Example 1 became slightly viscous but flowed after irradiation, uncured into glue. According to the comparison between Example 1 and Comparative Example 1, the photocurable hydrophilicity prepared by using the polymerizable photoinitiated monomer according to the present invention had a longer link chain and a tertiary amine structure that can participate in co-initiation, which showed a high curing efficiency and firmly gelling property after irradiation with ultraviolet light.

However, the above are only the preferred embodiments of the present invention. It will be apparent to those of skill in the art that variations may be applied according to the actual needs under the spirit of the present invention. Therefore, any equivalent changes and modifications made in accordance with the present invention should be still in the protection scope of the present invention.

The invention claimed is:

1. A photocurable hydrophilic polymer formed by copolymerization of a polymerizable photosensitive monomer and a hydrophilic monomer, wherein, the polymerizable photosensitive monomer comprises: 1) units containing a photosensitive structure; 2) units containing a tertiary amine co-initiator structure; 3) units containing an unsaturated bond, wherein the units containing the photosensitive structure are at least connected with the units containing the tertiary amine co-initiator structure through —OC(=O)—, and the units containing the unsaturated bond structure are connected with the units containing the photosensitive structure through the unit containing the tertiary amine co-initiator structure, wherein the molar fraction of polymerizable photosensitive monomer in the photocurable hydrophilic polymer is 0.05-10%, and the number average molecular weight of photocurable hydrophilic polymer is 2,000-1,500,000.

2. The photocurable hydrophilic polymer of claim 1, wherein the polymerizable photosensitive monomer has the structure of general formula (I):

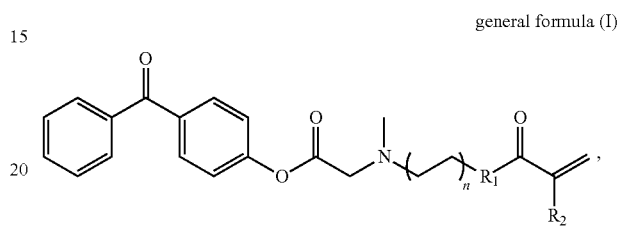

general formula (I)

wherein n is an integer of 1-20; $R_1$=O or NR, wherein R is H, a C1-C20 straight alkyl group, or a C3-C20 branched alkyl group; and $R_2$=H, a C1-C20 straight alkyl group, or a C3-C20 branched alkyl group.

3. The photocurable hydrophilic polymer according to claim 2, wherein n is 1 or 2.

4. The photocurable hydrophilic polymer of claim 1, wherein the hydrophilic monomer includes unsaturated carboxylic acid, unsaturated carboxylate, unsaturated carboxylic acid ester, unsaturated hydroxyalkyl ester, unsaturated polyether ester, unsaturated anhydride, unsaturated amide, unsaturated lactam and alkylene oxide, or a combination thereof.

5. The photocurable hydrophilic polymer of claim 4, wherein the hydrophilic monomer is selected from (meth) acrylic acid, (meth)acrylamide, vinyl pyrrolidone, hydroxyethyl(propyl) (meth)acrylate, polyethylene glycol methyl ether (meth) acrylate, dimethylacrylamide, or a combination thereof.

6. The photocurable hydrophilic polymer of claim 5, wherein the hydrophilic monomer is polyethylene glycol methyl ether (meth) acrylate.

7. The photocurable hydrophilic polymer of claim 1, wherein the molar fraction of polymerizable photosensitive monomer in the hydrophilic polymer is 0.5-10%.

8. The photocurable hydrophilic polymer of claim 7, wherein the molar fraction of polymerizable photosensitive monomer in the hydrophilic polymer is 0.5-5%.

9. The photocurable hydrophilic polymer of claim 8, wherein the molar fraction of polymerizable photosensitive monomer in the hydrophilic polymer is 0.8-1.5%.

10. The photocurable hydrophilic polymer of claim 1, wherein the number average molecular weight of photocurable hydrophilic polymer is 50,000-1,500,000.

11. The photocurable hydrophilic polymer of claim 10, wherein the number average molecular weight of photocurable hydrophilic polymer is 50,000-600,000.

12. A coating composition, comprising:
1) the photocurable hydrophilic polymer according to claim 1, wherein the photocurable hydrophilic polymer has a mass fraction of 0.1-20% based on the total amount of the coating composition; and 2) a solvent, wherein the solvent has a mass fraction of 60-99.9% based on the total amount of the coating composition.

13. The coating composition of claim 12, wherein the photocurable hydrophilic polymer has a mass fraction of 1-10% based on the total amount of the coating composition and the solvent has a mass fraction of 90-99% based on the total amount of the coating composition.

14. The coating composition of claim 13, photocurable hydrophilic polymer has a mass fraction of 3-5% based on the total amount of the coating composition and the solvent has a mass fraction of 95-98% based on the total amount of the coating composition.

15. The coating composition of claim 12, wherein the solvent includes water, low molecular weight alcohol, N,N-dimethylformamide, N,N-dimethylacetamide, dimethylsulfoxide, acetone, phenol, or a combination thereof.

16. The coating composition of claim 15, wherein the solvent is a mixture of water and ethanol.

17. The coating composition of claim 16, wherein the volume ratio of water to ethanol is 2:3-3:2.

18. A hydrophilic lubricating coating obtained by curing the coating composition of claim 12.

19. An article comprising at least one layer of the hydrophilic lubricating coating of claim 18.

20. The article of claim 19, wherein the article is a medical device.

\* \* \* \* \*